(12) United States Patent
Sanghera et al.

(10) Patent No.: US 8,244,349 B2
(45) Date of Patent: Aug. 14, 2012

(54) ADAPTIVE SHOCK DELIVERY IN AN IMPLANTABLE CARDIAC STIMULUS DEVICE

(75) Inventors: Rick Sanghera, San Clemente, CA (US); Jay A. Warren, San Juan Capistrano, CA (US)

(73) Assignee: Cameron Health, Inc., San Clemente, CA (US)

( * ) Notice: Subject to any disclaimer, the term of this patent is extended or adjusted under 35 U.S.C. 154(b) by 718 days.

(21) Appl. No.: 12/363,425

(22) Filed: Jan. 30, 2009

(65) Prior Publication Data

US 2009/0198296 A1    Aug. 6, 2009

Related U.S. Application Data

(60) Provisional application No. 61/025,780, filed on Feb. 2, 2008.

(51) Int. Cl.
*A61N 1/362* (2006.01)

(52) U.S. Cl. .......................................... 607/5

(58) Field of Classification Search ........................ 607/5
See application file for complete search history.

(56) References Cited

U.S. PATENT DOCUMENTS

| | | | |
|---|---|---|---|
| 4,589,420 A | 5/1986 | Adams et al. | |
| 5,224,475 A | 7/1993 | Berg et al. | |
| 5,224,476 A | 7/1993 | Ideker et al. | |
| 5,306,291 A | 4/1994 | Kroll et al. | |
| 5,324,309 A | 6/1994 | Kallok | |
| 5,468,254 A | 11/1995 | Hahn et al. | |
| 5,584,865 A | 12/1996 | Hirschberg et al. | |
| 5,593,427 A | 1/1997 | Gliner et al. | |
| 5,718,718 A | 2/1998 | Kroll et al. | |
| 5,728,139 A | 3/1998 | Post | |
| 5,735,879 A | 4/1998 | Gliner et al. | |
| 5,836,976 A * | 11/1998 | Min et al. | 607/6 |
| 6,029,086 A | 2/2000 | Kim et al. | |

(Continued)

FOREIGN PATENT DOCUMENTS

EP    1 304 137 A2    4/2003

(Continued)

OTHER PUBLICATIONS

International Search Report and Written Opinion for PCT/US2009/032783; issued Aug. 18, 2009.

*Primary Examiner* — Brian T Gedeon

(74) *Attorney, Agent, or Firm* — Pramudji Law Group PLLC; Ari Pramudji; Mark Schroeder

(57) ABSTRACT

Methods and devices that are configured to deliver cardiac stimuli in a particular fashion. In an illustrative embodiment, a method is used wherein a first stimulus is delivered using a first polarity, and, if the first stimulus fails to successfully convert an arrhythmia, a second stimulus having a second polarity that is different from or opposite of the first polarity is then delivered. Subsequent stimuli, if needed, are delivered in a continuing alternating-polarity manner. The first polarity may be determined by observing whether successfully-converting stimulus has been delivered previously and, if so, the polarity of the most recent stimulus that resulted in successful conversion is used as the first polarity. In additional embodiments, electrode configuration may be changed instead of or in addition to polarity, following unsuccessful stimulus delivery. Devices configured to perform such methods are included in additional illustrative embodiments.

6 Claims, 3 Drawing Sheets

U.S. PATENT DOCUMENTS

| | | |
|---|---|---|
| 6,185,459 B1 | 2/2001 | Mehra et al. |
| 6,647,292 B1 | 11/2003 | Bardy et al. |
| 6,721,597 B1 | 4/2004 | Bardy et al. |
| 6,865,417 B2 | 3/2005 | Rissmann et al. |
| 6,892,092 B2 | 5/2005 | Palreddy et al. |
| 6,952,608 B2 | 10/2005 | Ostroff |
| 6,988,003 B2 | 1/2006 | Bardy et al. |
| 2004/0215253 A1 | 10/2004 | Weinberg |
| 2006/0224225 A1 | 10/2006 | Ransbury et al. |
| 2007/0055314 A1 | 3/2007 | Bardy et al. |
| 2007/0179537 A1 | 8/2007 | Rissmann et al. |
| 2008/0045850 A1 | 2/2008 | Phillips |
| 2008/0154350 A1 | 6/2008 | Julian |

FOREIGN PATENT DOCUMENTS

| | | |
|---|---|---|
| EP | 1 304 137 A3 | 12/2004 |
| EP | 1 304 137 B1 | 5/2008 |
| WO | 00-09206 A1 | 2/2000 |

* cited by examiner

ADAPTIVE SHOCK DELIVERY IN AN IMPLANTABLE CARDIAC STIMULUS DEVICE

RELATED APPLICATIONS

The present application claims the benefit of and priority to U.S. Provisional Patent Application No. 61/025,780, filed Feb. 2, 2008 and titled ADAPTIVE SHOCK DELIVERY IN AN IMPLANTABLE CARDIAC STIMULUS DEVICE, the disclosure of which is incorporated herein by reference.

FIELD

The present invention relates to the field of implantable medical devices. More particularly, the present invention relates to implantable cardiac stimulus devices and methods of delivering stimulus with such devices.

BACKGROUND

Implantable cardioverter defibrillators (ICDs) can be beneficially used to automatically detect malignancies in patient cardiac function and cause cardiac function to return to normal or at least non-malignant function by delivering stimuli. Such abnormalities are often referred to as arrhythmias, and may include brady- or tachy-arrhythmias. Fibrillation is a tachyarrhythmia that may be atrial and/or ventricular in origin. Some arrhythmias such as ventricular fibrillation are considered malignant and warrant treatment by an ICD. There are many methods of detecting arrhythmias and determining whether an arrhythmia is malignant and therefore warrants treatment.

Once treatment is indicated, the goal is to convert a malignant arrhythmia to normal, or at least benign, cardiac rhythm by delivering one or more electrical stimuli, preferably in as short a time period as possible while conserving energy in response to these shockable conditions. An "episode" is a time period following identification of a shockable arrhythmia. During an episode, one or more stimuli may be delivered. An episode can terminate for several reasons including termination of the shockable condition (spontaneously or in response to stimulus) or identification of a timeout, such as when a predetermined maximum number of stimuli have been delivered. The present invention is aimed at improved and alternative devices and methods for delivering one or more stimuli in order to achieve successful conversion of malignant arrhythmias.

SUMMARY

The present invention includes methods and devices that are configured to deliver cardioversion and/or defibrillation stimuli. In an illustrative embodiment, a method is used wherein a first stimulus in an episode is delivered using a first polarity, and, if the first stimulus fails to end the episode, a second stimulus of the episode is delivered with a second polarity that is different from or opposite of the first polarity. Subsequent stimuli, if needed, are delivered in a continuing changing-polarity manner until the episode is terminated. The first polarity may be determined by observing whether successfully-converting stimulus has been delivered to terminate a prior episode and, if so, the polarity of the most recent stimulus that resulted in successful conversion is used as the first polarity. Some additional embodiments are further configured to modify the selection of electrodes for stimulus delivery. Implantable devices configured to perform such methods are included in additional illustrative embodiments.

DETAILED DESCRIPTION

The following detailed description should be read with reference to the drawings. The drawings, which are not necessarily to scale, depict illustrative embodiments and are not intended to limit the scope of the invention.

As used herein, the phrase "successfully convert" refers to causing an end to a malignant arrhythmia, such as a ventricular fibrillation or tachycardia, and causing the patient's heart to return to non-malignant cardiac operation. A complete return to "normal sinus" rhythm is not necessary for successful conversion. Successful conversion terminates an episode.

Figure 1A:
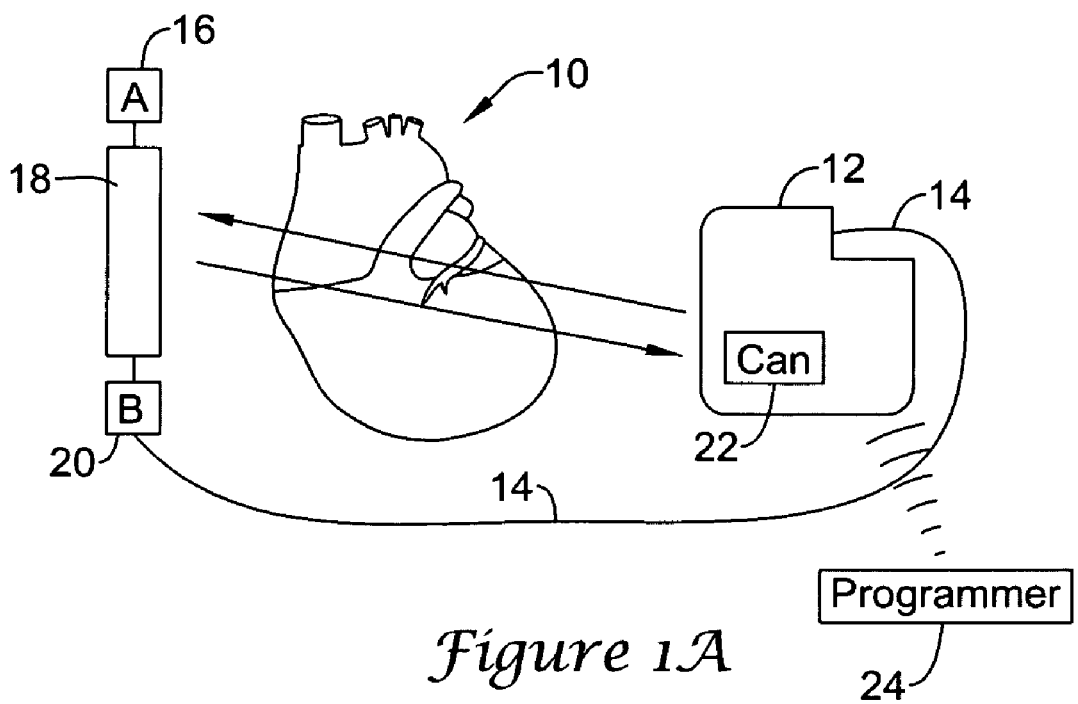
FIGS. 1A-1B are, respectively, illustrative subcutaneous and transvenous implantable cardiac stimulus systems.
Figure 1B:
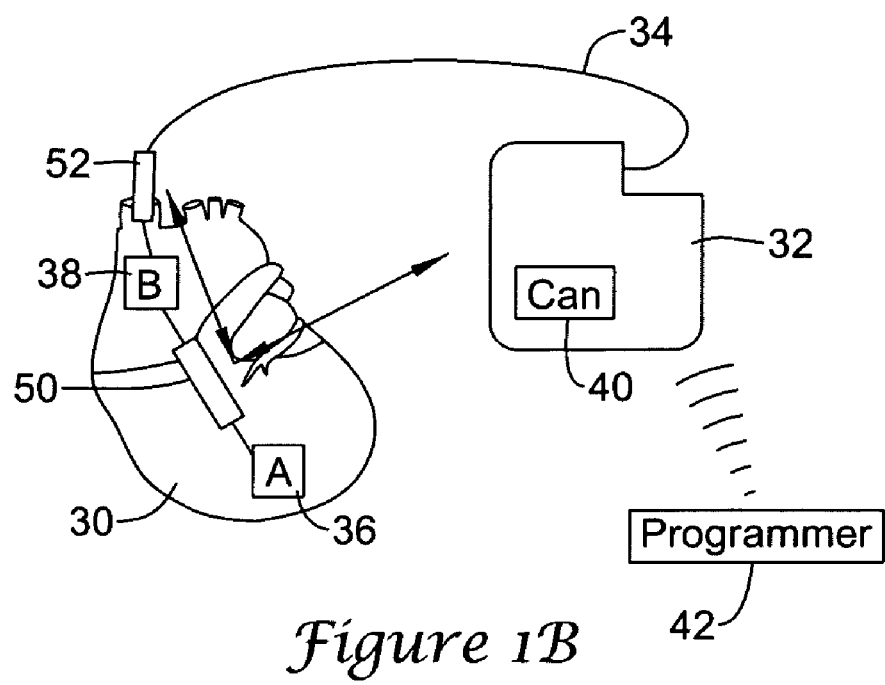

FIGS. 1A-1B, respectively, show subcutaneous and transvenous implanted cardiac stimulus systems relative to a patient's heart. The systems shown in FIGS. 1A-1B are merely illustrative. The present invention may be embodied in virtually any implantable cardiac stimulus system. For example, it may be embodied in transvenous or subcutaneous systems such as those shown in FIGS. 1A-1B, hybrid systems combining features of both, and/or systems using separately implanted devices that wirelessly communicate with one another. Additionally, the present invention may also be embodied in fully intravascular systems modeled on those shown in US Patent Application Publication Number 2006-0224225 to Ransbury et al.

Referring to FIG. 1A, the heart 10 is shown in relation to an implanted, subcutaneous cardiac stimulus system including a canister 12. A lead 14 is secured to canister 12 and includes sensing electrode A 16, a coil electrode 18, and sensing electrode B 20. A can electrode 22 is shown on the canister 12. An alternative subcutaneous system uses a flexible unitary housing rather than a can 12, with or without a lead. Illustrative subcutaneous systems are shown in U.S. Pat. Nos. 6,647,292 and 6,721,597, and the disclosures of these patents are incorporated herein by reference.

A vector for delivering cardiac stimulus is defined between the can electrode 22 and the coil electrode 18. Other vectors for stimulus delivery may be defined depending upon the internal circuitry of the device, different lead designs, and/or the size and shape of electrodes A and B 16, 20, which may also be used for stimulus delivery if so suited. The stimulus vector is illustrated as having two polarities.

Referring now to FIG. 1B, a transvenous system is shown relative to a patient's heart 30. The transvenous cardiac stimulus system includes a canister 32 connected to a transvenous lead 34. The lead 34 resides partly within the patient's vasculature, enters the patient's heart, and includes electrodes shown at 36, 38, 50 and 52 which may each be used for sensing and/or stimulus. The lead 34 may be anchored into the patient's myocardium. Rather than a single lead having several electrodes, separate atrial and ventricular leads may be used.

A can electrode 40 is shown on the canister 32. With this system, plural sensing and stimulus delivery vectors may be defined. The embodiment shown includes two stimulus delivery vectors each having two polarities, including stimulus vectors between electrodes 50 and 52 and between electrodes 40 and 50. Electrodes 40 and 52 may also be electrically linked as a single electric node for stimulus delivery. A third stimulus vector may also be defined between electrodes 40 and 52, although this is not shown in the illustration. Other lead and electrode configurations may also be used.

Each of the devices 12, 32 may further include such components as would be appropriate for communication (such as RF communication, inductive telemetry or other suitable communication linkage) with an external device such as a programmer. To this end, programmers 24 (FIG. 1A) and 42 (FIG. 1B) are also shown. For example, during an implantation procedure, once the implantable device 12, 32 and leads (if included) are placed, the programmer 24, 42 may be used to activate the implanted device 12, 32, and/or direct/observe diagnostic or operational tests. After implantation, the programmer 24, 42 may be used to non-invasively determine the status and history of the implanted device. The programmers 24, 42 in combination with the implanted devices 12, 32 may also allow interrogation for and annunciation of statistics, errors, history and potential problems to the user/medical practitioner, and may also allow for updating of programming in the implanted devices 12, 32.

A stimulus may take several forms, including monophasic and multiphasic (biphasic, triphasic, etc.) waveforms. For a multiphasic stimulus, the "polarity" of the stimulus is the polarity of the initial phase of energy delivery. For example, referring to FIG. 1A and defining the can electrode 22 as the positive electrode and the coil electrode 18 as the negative electrode, a positive polarity biphasic waveform begins with the can electrode 22 at a higher potential than the coil electrode 18 and then ends with the can electrode 22 at a lower potential than the coil electrode 18.

Figure 2:
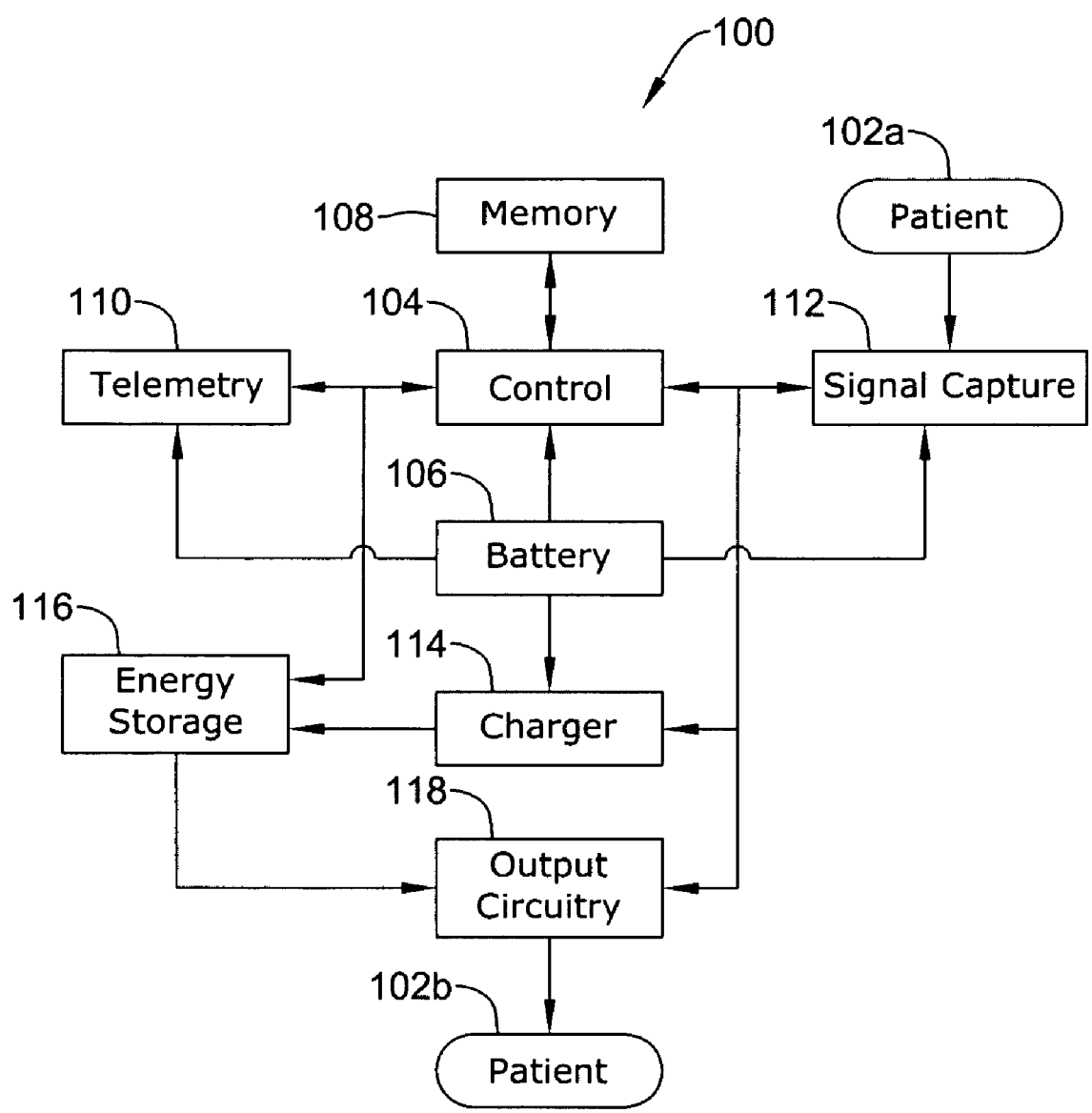
FIG. 2 is a functional block diagram for an illustrative example device.

FIG. 2 is a functional block diagram for an illustrative implantable cardiac stimulus device. In the illustrative example, operational circuitry for an implantable cardiac stimulus device is shown at 100, a patient is shown both at 102a and 102b. It should be understood that this is the same patient in both instances 102a, 102b, but the coupling electrodes may be different for each. For example, shock delivery electrodes may be separate or different from sensing electrodes, although this need not always be the case.

The operational circuitry includes a control block 104, which may take any suitable or conventional form. Microcontrollers and/or microprocessors may be used in control block 104. In addition to or as a replacement for a microcontroller or microprocessor, there may be various logic and other devices or subcircuits. A battery 106 is also included to power the control block 104, among other items. The control block 104 may access a memory 108, which may take various forms including RAM, ROM, Flash memory, or any other suitable form (optical, electrical, magnetic, etc.) for temporarily or permanently storing information and/or instruction sets. In some illustrative device embodiments, the control block 104 and/or the memory 108 are configured to perform the methods discussed and explained below with reference to FIG. 3.

The methods discussed herein may be embodied in any suitable manner, for example, in dedicated hardware and/or instruction sets for operating the operational circuitry and/or in the form of machine-readable media (optical, electrical, magnetic, etc.) embodying such instructions and instruction sets.

The operational circuitry 100 may also include telemetry 110, which may include such drivers, mixers, antenna(s), amplifiers and the like as are known for use in communications circuitry. Telemetry 110 is used to communicate with a programmer, such as programmers 24, 42 shown in FIGS. 1A-1B.

Signal capture block 112 includes amplifying and filtering circuitry which may take any form suitable for use in an implantable cardiac stimulus device for observing cardiac function. Signal capture block 112 may also including sampling and analog-to-digital devices, as well as local registers, memory or the like for temporarily storing captured information. A switch array may be provided to allow the signal capture block 112 to select a combination of sensing electrodes from the available electrodes in the system.

Generally speaking, the control block 104 uses the signal capture block 112 to capture data from the patient 102a. In response to instructions from telemetry 110 and/or instructions or data stored in memory 108, the control block 104 may analyze data from the signal capture block 112 to determine whether the patient 102a/b is in need of stimulus. If so, the control block 104 calls on the charger 114 to charge energy storage 116, which may include one or more capacitors in any suitable configuration. As is known to those of skill in the art, the charger 114 is used to step up the voltage from the battery 106 (often less than 10 volts) to a higher level (up to several hundred or even several thousand volts) for use in cardioversion or defibrillation.

The control block 104 and/or the charger 114 may monitor the voltage level on the energy storage 116 during charging to determine whether and when sufficient stimulus energy has been stored. Once enough energy is stored at energy storage 116 for stimulus delivery, the control block 104 manipulates output circuitry 118, which may include, for example, a plurality of switches and/or an H-bridge configuration, in order to deliver the stored energy to the patient 102b. A modified H-bridge type structure is shown, for example, in U.S. Pat. Nos. 6,865,417 and 6,952,608.

In an illustrative example, the control block 104 can manipulate the duration and form of the applied stimulus by controlling the output circuitry 118. For example, a monophasic, biphasic, or other waveform may be applied. The monophasic waveform generally comprises a duration of applied energy of a single output polarity. The biphasic waveform generally comprises first and second portions (often with a short pause therebetween), where the polarity switches (usually the polarity is reversed) from the first portion to the second portion. Definitionally, the "polarity" of a biphasic waveform refers to the polarity of the first portion of the waveform.

It is common for the amplitude of the applied voltage to drop during its application as the energy storage 116 (often a bank of capacitors) discharges energy. The change in output amplitude during an applied pulse is sometimes referred to as "tilt," a ratio of the final voltage to the initial voltage. Constant current and/or constant voltage stimuli may also be applied.

A patient's response to a stimulus may vary with the polarity of the stimulus. One measure of patient response is the defibrillation threshold (DFT), which is sometimes defined as the minimum threshold energy that needs to be applied to predictably convert a ventricular fibrillation to non-malignant cardiac rhythm. Results of a patient study using a subcutaneous system have shown that the DFT varies from patient to patient, and individual patients sometimes show a dramatic advantage for one polarity over the other. For example, in a sample of subcutaneous DFTs, 3 out of 11 patients showed a difference in DFT of more than 24 Joules for two opposing polarities using a single electrode pair, a large preference considering that 6 of the 11 patients had a least DFT of less than 21 Joules. Studies of transvenous DFT have also shown that some patients exhibit lower DFTs for one polarity or the other, while other transvenous patients display equal or similar DFTs regardless of polarity.

In addition to unpredictability across the population, DFTs can change over time within a given patient. This is particularly so if there are changes in patient pathophysiology and/or medication, for example. It is possible that a polarity which illustrates a substantially better DFT at the time of implant may not illustrate the same advantage at a later time.

Figure 3:
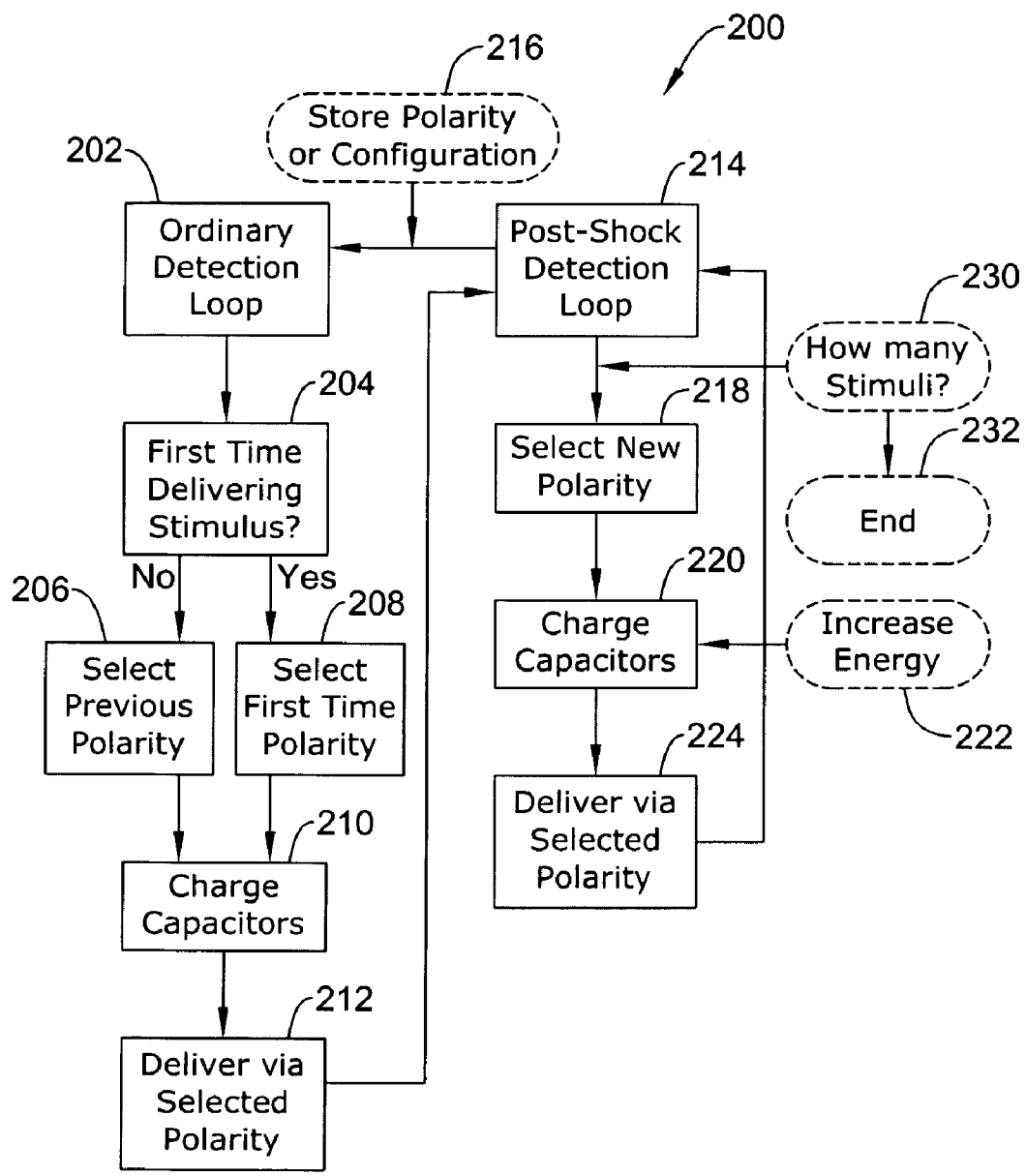
FIG. 3 is a block diagram for an illustrative method.

FIG. 3 is a block diagram for an illustrative method. The method 200 includes an ordinary detection loop, as shown at 202. The ordinary detection loop 202, for many implantable cardiac stimulus devices, will include a sequence of states in which the device monitors cardiac signals until a timeout occurs or until a captured signal exceeds a detection threshold. If the timeout occurs, analysis may be performed to determine whether stimulus is indicated since a predetermined amount of time (often several seconds) has passed since a most recent detected cardiac event. If an event is detected, the event and/or a series of previously detected events may be analyzed using various methods to determine whether cardiac stimulus is appropriate.

In some methods, an event detection leads to analysis of event rate. If the event rate exceeds some threshold (thresholds may vary by patient), it may be determined that the patient is experiencing a tachyarrhythmia and further analysis may be performed to determine whether cardiac stimulus is appropriate. In some methods, an event detection causes a portion of cardiac signal around or adjacent to the event to be recorded, and the recorded data may be undergo morphological analysis to determine whether the event itself indicates a malignant cardiac condition. In any of these scenarios, the loop 202 may continue until it is determined that cardiac stimulus is warranted. Any suitable method and/or devices may be used in the loop 202; the present invention is directed at what occurs after it is determined that cardiac stimulus is warranted.

Once it is determined in loop 202 that cardiac stimulus is warranted, the method continues to block 204, where it is determined whether the impending stimulus delivery is the first time stimulus will be delivered by the system. If stimulus delivery has been delivered previously, the method continues at 206 where the polarity of a previous stimulus is selected. In one illustrative example, the method selects the polarity of a previous stimulus that caused the patient's heart to successfully convert to a non-malignant cardiac state. The method may select the polarity of only the most-recent of such successfully-converting stimuli, if more than one has been delivered.

In some embodiments, in addition to or as an alternative to polarity, electrode configuration may be stored and/or modified. Referring to FIG. 1A, the shocking configuration may be modified from one of coil electrode 18 and can electrode 22 to use a different configuration selecting two or more of electrodes A 16, coil 18, B 20 and Can 22. In yet another embodiment, one or more initial stimuli are applied using monophasic waveforms, and, if the monophasic waveform(s) fail to achieve successful conversion, the device configuration is changed to use a multiphasic waveform, such as a biphasic waveform.

It should be noted that as used herein, modifying the electrode configuration is distinguished from modifying the energy level. However, some illustrative embodiments may modify energy levels in addition to modifying shock electrode configuration. For example, one embodiment increases energy levels after a failed attempt at conversion. Yet another embodiment modifies energy levels when changing the shock electrode configuration to accommodate changes in generated electric field, relative to the heart, that may result from changes to the electrode configuration.

In an alternative embodiment, if several previous successfully-converting stimuli have been delivered, a "majority-rule" may be used to select the polarity that has been successful most often. This may entail keeping track of prior stimulus applications in terms of success, polarity and, if desired, any other suitable characteristics.

In another embodiment, an implementation may include the use of a register to keep track of stimulus configuration, which may include electrode selection and/or polarity. For example, the shock configuration register may store a value until a shock is delivered. If the shock is successful, the shock configuration register is left as is, and if the shock is unsuccessful, the stored value in the shock configuration register is changed to correlate to at least one of a different configuration and/or a different polarity.

If no previous stimuli have been delivered and the first episode is occurring, then the method uses step 208, where a first time polarity is selected. The first time polarity selection at step 208 may be performed in several ways. For example, first time polarity may be preprogrammed or it may be programmed by an implanting medical practitioner at the time of implant. First time polarity may also be programmed at or after implant by an overseeing medical practitioner. The selection and configuration of electrodes may be pre-programmed and retrieved as well.

After, or even during steps 204 and 206/208, the system charges one or more capacitors, as shown at 210, which are part of the energy storage 116 (FIG. 2). Once the capacitor(s) are sufficiently charged during step 210, stimulus is delivered at step 212 using the polarity that was selected in either of steps 206, 208. In some embodiments, an additional step may be provided in which a double check of the continued malignant cardiac arrhythmia is performed between steps 210 and 212, such that, if there is a spontaneous conversion to ordinary rhythm, unnecessary stimulus delivery is prevented.

After stimulus delivery at step 212, the method continues to a post-shock detection loop shown at 214. In some embodiments, following stimulus delivery, different variables, values, and methods may be used than would occur in the ordinary detection loop. This need not be the case; if desired, the post-shock detection loop 214 may resemble the ordinary detection loop 202.

If the post-shock detection loop 214 finds a return to non-malignant cardiac operation, the episode is terminated and the method returns to the ordinary detection loop 202. During this step, the polarity and/or configuration for the shock delivery may be stored, as indicated at 216. If desired, the energy used during delivery of a successful stimulus may also be stored when returning to the ordinary detection loop 202.

If, instead, the post-shock detection loop 214 finds a continuing malignant arrhythmia, the method continues to step 218. At step 218, a new polarity is selected, with the polarity being different or opposed to the previously used polarity. The capacitors are charged, as shown at 220. This may include increasing the energy being stored, as indicated at 222, since this step would be reached only after an unsuccessful stimulus. In addition to changes in energy level and/or polarity, the electrode configuration may also be changed. Then, stimulus is delivered, as shown at 224. As before, a double-check step to confirm the malignant rhythm may be performed before stimulus delivery in step 224.

If the post-shock detection loop 214 repeatedly finds a malignant cardiac arrhythmia persists even after stimulus, the method terminates after a threshold number of stimuli have been delivered in consecutive fashion, that is, without returning to the ordinary detection loop 202. This is shown at 230, 232. In some illustrative embodiments, the threshold is 4-10 stimuli, although this may vary.

As noted above, in some embodiments, a method may be used within a system having more than two electrodes that are configured for delivery of stimuli. For example, a subcutaneous system may include three stimulus delivery electrodes (one on the canister and two on the lead, or two on an elongated canister and one on the lead, for example), and pairs of electrodes or configurations of three electrodes (i.e., two cathodes and one anode) may be enabled by the use of switching circuitry within the device. Illustrative systems are shown, for example, in U.S. Pat. No. 6,988,003 to Bardy et al., which is incorporated herein by reference. Likewise, the transveneous system shown in FIG. 1B includes three stimulus delivery electrodes.

After shock delivery with one configuration, a different configuration of the electrodes may be selected, rather than a change in polarity. In such a case, information as to the configuration used to successfully convert a patient's malignant arrhythmia, in addition to or in place of just the polarity, may be stored for future reference. Such configurations may also include information related to the amplitude, shape, and/or duration of the stimulus applied.

In some illustrative embodiments, if a first delivered therapy fails to convert the patient successfully, one or more successive therapy deliveries follow. The use of successive therapy deliveries can include storing indicia of therapy configurations that have been attempted and failed. For future use, those therapy configurations that have previously failed may be placed in a queue such that un-used configurations will be exhausted before a previously failing configuration is re-attempted.

Those skilled in the art will recognize that the present invention may be manifested in a variety of forms other than the specific embodiments described and contemplated herein. Accordingly, departures in form and detail may be made without departing from the scope and spirit of the present invention.

What is claimed is:

1. An implantable cardioverter-defibrillator (ICD) system including a lead system coupled to a canister, the canister housing operational circuitry, the ICD comprising:
    a plurality of stimulus delivery electrodes consisting of a first electrode disposed on the lead system and a second electrode that takes the form of an electrically conductive surface that makes up all or a portion of the surface of the canister;
    implantable operational circuitry coupled to the first and second electrodes such that first and second selectable stimulus delivery configurations are available for use by the operational circuitry;
    the improvement comprising:
    the operational circuitry being configured to determine whether stimulus is currently needed and if so, delivering the currently needed stimulus by:
        determining whether a successful stimulus has previously been delivered; and, if so, using a stimulus delivery configuration for a most recent successful stimulus delivery to deliver the currently needed stimulus;
        otherwise delivering the currently needed stimulus using a predetermined stimulus delivery configuration chosen from the first and second configurations;
    wherein:
        the operational circuitry is configured to provide therapy as a biphasic waveform having first and second phases;
        the first configuration uses the first electrode as the positive electrode during the first phase of the biphasic waveform and as the negative electrode during the second phase of the biphasic waveform; and
        the second configuration uses the second electrode as the positive electrode during the first phase of the biphasic waveform and as the negative electrode during the second phase of the biphasic waveform.

2. The ICD system of claim 1 wherein the operational circuitry is configured such that: if it is determined that a prior successful stimulus has been delivered, the operational circuitry selects an energy level for output stimulus equal to that used in the successful stimulus; otherwise, the operational circuitry selects a predetermined energy level for output stimulus.

3. A method of treating a patient using an implantable cardioverter defibrillator (ICD) having a plurality of electrodes and operational circuitry configured to detect malignant arrhythmias; the plurality of electrodes including a coil electrode disposed on a lead and an electrically conductive canister for the ICD, with the operational circuitry comprising therapy output circuitry including a first output and a second output, the therapy output circuitry being coupled to the electrically conductive canister and the coil electrode, wherein the operational circuitry is configured to enable only first and second configurations to deliver stimulus using the electrically conductive canister and the coil electrode; the method comprising:
    detecting, using the plurality of electrodes, a malignant arrhythmia and determining therapy is indicated;
    a) determining whether a prior therapy has been delivered by the ICD to successfully convert a prior malignant arrhythmia and, if so, re-using whichever of the first configuration or the second configuration was used in delivering the successfully converting prior therapy to deliver therapy; or
    b) determining that no prior successful therapy has been delivered and using a predetermined therapy configuration chosen from the first and second configurations to deliver therapy;
    determining whether the delivered therapy from one of steps a) or b) successfully converts the malignant arrhythmia and:
        if the delivered therapy is successful, storing data relating to the configuration of the successful delivered therapy; or
        if the delivered therapy is not successful, delivering therapy by switching to the other of the first and second configurations and until therapy is successful or until a timeout occurs.

4. The method of claim 3 wherein the stimulus electrodes are disposed within a patient without contacting or entering the patient's heart.

5. The method of claim 3 wherein if the delivered therapy is not successful, the method further comprises raising the energy level delivered by a subsequent therapy in addition to changing the electrode configuration.

6. A method of patient treatment comprising:
    providing an implantable cardioverter-defibrillator (ICD) comprising a lead electrode assembly coupled to a canister that houses operational circuitry for the ICD, the lead electrode assembly including a stimulus electrode and the canister having a stimulus electrode for use in conjunction with the stimulus electrode on the lead electrode assembly, wherein the ICD is configured to define first and second therapy configurations using the stimulus electrode on the lead and the stimulus electrode on the canister, each configuration for delivering biphasic stimulus, such that in the first configuration the stimulus electrode on the lead electrode assembly is the positive electrode in the first phase of the biphasic stimulus and in the second configuration the stimulus electrode on the canister is the positive electrode in the first phase of the biphasic stimulus;

implanting the ICD into the patient such that the canister is disposed subcutaneously outside the patient's ribcage and the lead electrode assembly does not contact or enter the patient's heart;

the operational circuitry observing electrical cardiac activity of the patient to determine whether a malignant arrhythmia is occurring;

if a malignant arrhythmia is identified by the operational circuitry:

a) the operational circuitry preparing to deliver electrical therapy to the patient by charging a capacitor to an energy level chosen for therapy;

b) the operational circuitry observing whether a previous successful therapy delivery using one of the first therapy configuration or the second therapy configuration has occurred and, if so, the operational circuitry enabling a therapy configuration corresponding to the previous successful therapy delivery, otherwise the operational circuitry enabling a predetermined one of the first therapy configuration or the second therapy configuration chosen for initial therapy delivery;

c) the operational circuitry delivering therapy to the patient via the therapy delivery electrodes; and d) if the malignant arrhythmia does not terminate in response to the delivered therapy, changing a configuration of the therapy delivery to the other of the first therapy configuration or the second therapy configuration which was not enabled in step (b) and delivering an additional therapy until:

therapy delivery succeeds in converting the malignant arrhythmia, at which point the method also includes storing the configuration of the therapy delivery that succeeds; or a timeout occurs and therapy delivery is terminated.

\* \* \* \* \*